United States Patent [19]

Hani et al.

[11] Patent Number: 6,162,446

[45] Date of Patent: Dec. 19, 2000

[54] IN-SITU GENERATION OF ZINC PYRITHIONE IN PERSONAL CARE COMPOSITIONS

[75] Inventors: Rahim Hani, Cheshire; George A. Polson, Harwinton, both of Conn.

[73] Assignee: Arch Chemicals, Inc., Norwalk, Conn.

[21] Appl. No.: 09/038,026

[22] Filed: Mar. 11, 1998

[51] Int. Cl.⁷ ...................................................... A61K 7/00
[52] U.S. Cl. ..................... 424/401; 424/489; 424/DIG. 4; 514/358; 514/852
[58] Field of Search ..................................... 424/401, 489, 424/DIG. 4; 514/852, 358

[56] References Cited

U.S. PATENT DOCUMENTS

| | | | |
|---|---|---|---|
| 2,809,971 | 10/1957 | Bernstein et al. | 260/270 |
| 3,159,640 | 12/1964 | McClure et al. | 260/294.8 |
| 4,940,578 | 7/1990 | Yoshihara et al. | 424/70 |
| 5,540,860 | 7/1996 | Hosseini et al. | 252/308 |
| 5,540,920 | 7/1996 | Vinopal et al. | 424/405 |
| 5,650,095 | 7/1997 | Hosseini et al. | 252/308 |

*Primary Examiner*—S. Mark Clardy
*Assistant Examiner*—Michael A. Williamson
*Attorney, Agent, or Firm*—Dale Lynn Carlson; Todd E. Garabedian; Wiggin & Dana

[57] ABSTRACT

Disclosed is a personal care composition comprising: (a) water or an alcohol, (b) at least one dispersant or surfactant, and (c) as an antimicrobial or preservative additive, particles of an in-situ transchelation reaction product of a zinc compound selected from the group consisting of zinc salts of organic acids, zinc salts of inorganic acids, zinc hydroxide, zinc oxide, and combinations thereof, said zinc compound being soluble in said water or alcohol, with pyrithione acid or a pyrithione salt that is soluble in said water or alcohol. Also disclosed is a process for preparing the personal care composition, and a coated substrate containing a coating of the personal care composition.

23 Claims, No Drawings

IN-SITU GENERATION OF ZINC PYRITHIONE IN PERSONAL CARE COMPOSITIONS

FIELD OF THE INVENTION

This invention relates generally to zinc pyrithione-containing personal care compositions, and more particularly to methodology for preparing these compositions using in-situ transchelation of a soluble pyrithione salt with pyrithione acid or a soluble pyrithione salt.

BACKGROUND OF THE INVENTION

Sodium pyrithione (also called the sodium salt of 1-hydroxy-2-pyridinethione, sodium pyridine-2-thiol-N-oxide, or 2-pyridinethiol-1-oxide, Na salt) has excellent antimicrobial properties, and is a well-known commercial product typically employed as a biocide and preservative in functional fluids, such as metalworking fluids, lubricants, cosmetics and toiletries. Sodium pyrithione is commonly made by reacting 2-chloropyridine-N-oxide with NaSH and NaOH, as disclosed, for example, in U.S. Pat. No. 3,159,640.

Likewise, zinc pyrithione [also known as zinc pyridine-2-thiol-N-oxide or bis [1-hydroxy-2(H) pyridinethionato]-zinc] is a broad-spectrum antimicrobial agent and preservative in metalworking fluids, plastics, paints, adhesives and cosmetics. One of the principal applications for zinc pyrithione is its use as an anti-dandruff agent in shampoo.

Zinc pyrithione is typically made at the sodium pyrithione production plant by reacting sodium pyrithione with a zinc salt, such as zinc sulfate, to form a zinc pyrithione precipitate, as disclosed, for example in U.S. Pat. No. 2,809,971, which is typically washed and then dispersed in water to form an aqueous dispersion of zinc pyrithione in water. This conversion of sodium pyrithione to form the zinc pyrithione dispersion at the pyrithione manufacturing plant is labor intensive. Moreover, the resulting zinc pyrithione dispersion is subject to settling problems, inasmuch as the zinc pyrithione tends to physically settle out of the dispersion during shipment or storage prior to use of the dispersion. This settling problem necessitates mixing of the dispersion by the manufacturer of personal care compositions containing the dispersion in order to insure homogenity of the dispersion in the composition. In addition, the settling problem can result in "caking" of the zinc pyrithione in the bottom of the drum in which it is stored and shipped, particularly when this product is stored for several months or subjected to wide fluctuations in ambient temperature.

In view of the above, it should be clear that there is a need for improved methodology for preparing zinc pyrithione-containing personal care compositions without risking the zinc pyrithione dispersion settling problems encountered heretofore. The present invention provides one solution to this need.

SUMMARY OF THE INVENTION

In one aspect, the present invention relates to a process for preparing a zinc pyrithione-containing personal care composition which comprises reacting, in a personal care composition, pyrithione acid or a pyrithione salt other than zinc pyrithione, or a combination thereof, with a zinc compound that is soluble in the personal care composition, said zinc compound being selected from the group consisting of zinc salts of organic acids, zinc salts of inorganic acids, zinc hydroxide, zinc oxide, and combinations thereof, said zinc compound being soluble in the personal care composition, thereby causing in-situ transchelation of the pyrithione salt with the zinc salt to form said zinc pyrithione-containing personal care composition. Pyrithione salts useful as reactants in this process include magnesium pyrithione, strontium pyrithione, copper pyrithione, zinc pyrithione, cadmium pyrithione, zirconium pyrithione, and combinations thereof. Zinc salts useful as reactants in this process include zinc sulfate, zinc chloride, zinc acetate, and combinations thereof.

In another aspect, the present invention relates to a process for preparing a zinc pyrithione-containing personal care composition selected from the group consisting of shampoo, soap, skin care medicament, and combinations thereof, said process comprising contacting water or an alcohol with at least one surfactant and with a transchelation product produced by reacting pyrithione acid or a pyrithione salt that is soluble in the personal care composition, or a combination thereof, with a zinc compound selected from the group consisting of zinc salts of organic acids, zinc salts of inorganic acids, zinc hydroxide, zinc oxide, and combinations thereof, said zinc compound being soluble in the personal care composition.

In yet another aspect, the present invention relates to a personal care composition comprising:

(a) water or an alcohol, (b) at least one dispersant or surfactant, and (c) as an antimicrobial or preservative additive, particles of an in-situ transchelation reaction product of a zinc compound selected from the group consisting of zinc salts of organic acids, zinc salts of inorganic acids, zinc hydroxide, zinc oxide, and combinations thereof, said zinc compound being soluble in said water or alcohol, with pyrithione acid or a pyrithione salt that is soluble in said water or alcohol. Preferably, component (a) is present in said personal care composition in an amount of from about 5% to about 70%, component (b) is present in an amount of from about 2% to about 50%, and component (c) is present in an amount of from about 0.1% to about 2%, based upon the weight of said personal care composition, with the proviso that the total of said component (a) plus said component (b) plus said component (c) does not exceed 100%. The reaction product is suitably in the form of solid particles in the personal care composition, and these solid particles are advantageously amorphous or crystalline particles in a shape selected from the group consisting of rods, needles, cubes, platelets, and combinations thereof.

In still another aspect, this invention relates to a coated substrate comprising a substrate selected from the group consisting of skin, hair and combinations thereof, and a coating on said substrate, said coating comprising particles of zinc pyrithione, said particles being produced by an in-situ transchelation reaction of pyrithione acid or a soluble pyrithione salt with a zinc compound selected from the group consisting of zinc salts of organic acids, zinc salts of inorganic acids, zinc hydroxide, zinc oxide, and combinations thereof.

These and other aspects will become apparent upon reading the following detailed description of the invention.

DETAILED DESCRIPTION OF THE INVENTION

It has now been surprisingly found in accordance with the present invention that the in situ formation of zinc pyrithione, either in a personal care composition or in a precursor component of the personal care composition, provides several advantages over the prior art use of preformed zinc pyrithione in these formulations. First, the present invention overcomes the above-discussed settling problem associated with aqueous dispersions of zinc pyrithione, since the zinc pyrithione is formed in situ in the personal care composition. The in situ-formed zinc pyrithione particles are found to be stable in the personal care composition. These compositions (e.g., liquid, gel or creme shampoos, liquid, gel or creme skin care medicaments, and liquid, gel or creme soaps) typically contain one or more surfactants, and have a relatively high viscosity. This high viscosity and the presence of surfactant(s) insure that the in situ prepared zinc pyrithione is stable against settling in the personal care composition. Second, shipment of a pyrithione solution (e.g., aqueous sodium pyrithione) to the personal care product manufacturer eliminates the likelihood of a freezing/settling problem that exists when shipping zinc pyrithione dispersion to the personal care product manufacturer. Third, in view of the high solubility of sodium pyrithione in water and in alcohol, relative to the much lower solubility of zinc pyrithione in these fluids, the sodium pyrithione can be shipped in higher concentrations in these fluids, as compared to zinc pyrithione. For example, a solution of up to 50% by weight of sodium pyrithione in water is suitably prepared and utilized in the process and composition of the present invention, whereas commercial dispersions of aqueous zinc pyrithione typically require 60% by weight of water, thus allowing for only 40% by weight of zinc pyrithione. This enables the pyrithione manufacturer to ship less water to the personal care composition manufacturer, thus saving on shipping costs.

The reactants employed to prepare zinc pyrithione in situ in the personal care composition, in accordance with the present invention, are suitably selected to provide not only the zinc pyrithione, but also a thickening agent for the personal care composition. By way of illustration, sodium chloride is commonly used as a thickening agent in personal care compositions. By selecting zinc chloride and sodium pyrithione for in-situ transchelation in the personal care composition, or in its precursor, to form the desired zinc pyrithione, sodium chloride is also formed, providing the added bonus of a thickening agent in the composition. Other useful thickening agents that are produced in situ in an analogous fashion include ammonium chloride and sodium sulfate. On the other hand, if it is desired to have no salt, other than zinc pyrithione, incorporated into the personal care composition by virtue of the transchelation reaction, then pyrithione acid and zinc oxide or zinc hydroxide are suitably employed as the transchelation reactants. These reactants produce only zinc pyrithione and water as reaction products.

The zinc compound used as a transchelation reactant in accordance with the present invention is suitably selected from the group consisting of zinc salts of organic acids, zinc salts of inorganic acids, zinc hydroxide, zinc oxide, and combinations thereof, with the proviso that the zinc compound is soluble in the personal care composition. Illustrative zinc salts include zinc chloride, zinc sulfate, zinc acetate, and combinations thereof. Zinc chloride is preferred. The term "soluble in the personal care composition" is intended to denote that the zinc compound is soluble in the personal care composition in an amount of at least 100 ppm, preferably at least 1000 ppm.

The pyrithione reactant used in the process and composition of this invention is suitably a pyrithione salt, such as sodium pyrithione, potassium pyrithione, lithium pyrithione, chitosan pyrithione, magnesium disulfide pyrithione, ammonium pyrithione, combinations thereof, and the like, or pyrithione acid, having the structure

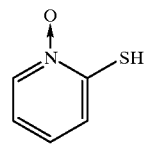

or a combination thereof. The preferred pyrithione salt is sodium pyrithione.

Although the molar ratio of the pyrithione reactant relative to the zinc compound is not narrowly critical, it is preferred that between 1 and 1.5 moles of zinc compound be employed per 2 moles of pyrithione used. The amount of pyrithione acid or water-soluble salt of pyrithione that is soluble in the transchelation reaction mixture can vary over a wide range. A preferred amount of pyrithione or water-soluble pyrithione salt is from about 1% to about 50% by weight, based upon the total weight of the reaction mixture.

Useful reaction media for the transchelation reaction of the present invention include water, organic solvents, and combinations thereof. Useful organic solvents include alcohols, such as methanol, ethanol, amines such as diethanolamine, ethers, esters, and the like.

Additional materials, such as dispersants, dispersant/surfactant blends, and the like may be added to the reactants either before, or during, the precipitation reaction to prevent agglomeration of the pyrithione salt particles formed by virtue of the reaction, if desired. Alternatively or additionally, a dispersant or other dispersing agent providing dispersing characteristics to the particles of pyrithione salt formed during the transchelation reaction, may be added at the completion of the reaction to prevent particle agglomeration. Exemplary dispersants include sodium salts of polymerized alkyl naphthalene sulfonic acids such as "DARVAN" (R. T. Vanderbilt), "DEMOL N" (Kao Chemicals), "DAXAD 11" (Hampshire Chemicals), or "TAMOL N" (Rohm and Haas).

The dispersant is suitably used alone or in combination with a surfactant. Suitable surfactants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. If desired, the alcohol alkoxylate is suitably end-capped with a lower alkyl group, and such a product is commercially available as POLY-TERGENT® SLF-18 available from Olin Corporation.

Useful anionic surfactants, that are suitably employed in the compositions of the present invention, include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates.

Other useful anionics are polycarboxylated alcohol alkoxylates, preferably those selected from the group consisting of the acids or organic or inorganic salts of the following: polycarboxylated linear alcohol alkoxylates, polycarboxylated branched alcohol alkoxylates, polycarboxylated cyclic alcohol alkoxylates, and combinations thereof.

Illustrative cationic surfactants include alkyl triammonium halide, non-linear alkyl dimethyl halide and alkyl dimethyl benzyl ammonium halide-containing surfactants.

Illustrative amphoteric dispersants include polyglycol ether derivatives, ethoxylate oxazolin derivatives, lauramidopropyl betain and lecithin.

As will be appreciated by those skilled in the art, suitable blends can be employed in the process of the present invention based on various combinations of the above-described surfactants. The dispersant or dispersant/surfactant blend is preferably employed in a total amount of between about 0.05 and 10%, more preferably between about 0.1 and 5%, most preferably between about 0.5 and about 1.5% by weight, based on the total weight of the reaction mixture.

The personal care compositions of the present invention suitably also contain thickening agents. Illustrative thickening agents include cellulose 30 derivatives, for example methyl, hydroxyethyl, hydroxypropyl and carboxymethyl cellulose, poly(vinyl alcohol), poly(vinylpyrolidone), poly(ethyleneglycol), salts of poly(acrylic acid) and salts of acrylic acid/acrylamide copolymers.

In order to increase the stability against freezing, electrolytes there may be included in the personal care composition. Suitable electrolytes include monomers, such as 1,2-diols, for example glycol, 1,2-propylene glycol and 1,2-butylene glycol, or polymers thereof, or ethoxylated compounds. For example reaction products of ethylene oxide with long-chain alkanols, amines, alkyd phenols, poly(propyleneglycol), or poly(butylene glycol), or a combination thereof, or the like.

The minimum temperature of film formation may be reduced by adding solvents, such as ethylene glycol, butyl glycol, ethyl glycol acetate, ethyl diglycol acetate, butyl diglycol acetate, benzene or alkylated aromatic hydrocarbons. As defoaming agents there are suitable for example poly(propylene glycol) and polysiloxanes. Optionally other antimicrobial additives can additionally be incorporated into the personal care compositions of the present invention. Illustrative of such other antimicrobial additives are polymyxin E, polymyxin B, lower alkyl esters of para-hydroxybenzoic acid (so-called "parabens"), salts thereof, and combinations thereof. These optional other antimicrobial additives are suitably employed in a weight ration of from 1 to 10,000 to 10,000 to 1, based upon the amount of pyrithione employed in the personal care composition. Useful optional solvents include methylisobutylketone (herein referred to as "MIBK"), xylene, ethyl benzene, methanol, and combinations thereof.

The temperature employed in the transchelation reaction in accordance with the present invention is suitably from about 0° C. and about 100° C., preferably from about 20° C. and about 90° C. The pressure employed in the reaction is suitably between one and two atmospheres, although higher pressures may be employed if desired. Advantageously, this reaction can be run at room temperature (i.e., 20° C. to 25° C.), and atmospheric pressure.

The personal care compositions prepared in accordance with the present invention to contain dispersed particles of zinc pyrithione are suitably employed in any of a variety of personal care applications, in a liquid or spreadable solid form, alone or in combination with an inert carrier such as water, liquid hydrocarbons, ethanol, isopropanol, or the like. They can be employed using conventional procedures to control bacteria and fungi on substrates such as the skin or hair, and can be applied in an antimicrobial amount by conventional procedures such as spraying, dipping, drenching impregnation, and the like. On the substrate, as well as in the personal care composition, the particles of zinc pyrithione suitably have a shape selected from the group consisting of platelets, rods, needles, cylinders, cones, ellipsoids, prisms, parallelepipeds, pyramids, cubes, and combinations thereof. These particles of zinc pyrithione are suitably crystals having a configuration selected from triclinic, monoclinic, orthorhombic, tetragonal, cubic, trigonal, hexagonal now have a shape selected from the group consisting of platelets, rods, needles, cylinders, cones, ellipsoids, prisms, parallelepipeds, pyramids, cubes, and combinations thereof.

Illustrative examples of typical shampoo formulations follow: A typical antidandruff shampoo comprises the following:

(a) Water in an amount of 43.8%

(b) Zinc pyrithione in an amount of 3%

(c) Cocamide DEA in an amount of 1%

(d) Triethanolamine lauryl sulfate in an amount of 40%

A typical premium antidandruff shampoo comprises the following:

(a) Deionized water in an amount of 76%

(b) Di(hydrogenated) tallow phthalic acid amide in an amount of 5%

(c) Preservative (d) Citric acid, 50% aq soln OR sodium hydroxide (50% soln)

(e) Ammonium chloride

A typical antidandruff shampoo with Conditioner is the following:

(a) Deionized water in an amount of 76%

(b) Di(hydrogenated) tallow phthalic acid amide in an amount of 5%

(c) Preservative (d) Citric acid, 50% aq soln. OR sodium hydroxide (50% soln)

(e) Ammonium chloride

Another typical antidandruff shampoo with conditioner is the following:

(a) Deionized water in an amount of 23.85%

(b) Sodium laureth sulfate in an amount of 30%

(c) Tricetylammonium chloride in an amount of 0.50%

(d) Cocamide MEA in an amount of 1.70%

(e) Preservative in an amount of 0.05%

(f) Citric acid, 25% aqueous solution

An "extra body" antidandruff shampoo is the following:

(a) Deionized water in an amount of 64.6%

(b) Methyl Paraben in an amount of 0.30%

(c) Triethanolamine lauryl sulfate in an amount of 20%

(d) Cocodimonium hydrolyzed animal protein in an amount of 1%

(e) FD&C Blue No. 1

(f) Citric acid, 50% aq soln.

The following examples are intended to illustrate, but in no way limit the scope of, the present invention. Unless otherwise stated, the "parts" and "%" are "parts by weight" and "percent by weight", respectively.

EXAMPLE 1

Transchelation of Zinc Chloride with Sodium Pyrithione In-situ in a Shampoo to Produce Zinc Pyrithione Particles in Cube Form in the Shampoo A sample of a commercial shampoo of the two-in-one shampoo-and-conditioner type was gently heated to about 60° C. with constant stirring. The shampoo contained the following ingredients in the approximate amounts specified in weight percent based upon the weight of the shampoo: about 40% of water, about 20%–30% of ammonium laureth sulfate surfactant, about 15% of ammonium lauryl sulfate surfactant, glycol distearate, dimethicone, fragrance, ammonium xylenesulfonate, about 3% of cocamide MEA foam stabilizer, from 2% to 4% of cetyl alcohol and stearyl alcohol, about 0.5% of polyquarternium-10 conditioner, about 1% mineral oil lubricant, sodium phosphate, stearyl alcohol, about 0.5% of DMDM hydantoin preservative, about 1% of sodium phosphate and disodium phosphate buffer, sodium chloride thickener, and FD&C yellow no. 10 and FD&C blue no.1. An aqueous solution of zinc chloride was mixed into the heated shampoo. With stirring, an aqueous solution of the sodium salt of 2-mercaptopyridine-N-oxide was added over a period of 30 minutes. The stoichiometry of the reactants was such that there was a slight excess of zinc chloride. The mixture was stirred to ensure homogeneity and cooled to ambient temperature. A sample of the shampoo with in situ prepared zinc salt of 2-mercaptopyridine-N-oxide was analyzed the particle size and shape of the crystals formed by scanning electron microscopy (SEM). The particles were found to be cubes having dimensions of about 5 by 5 by 5 microns.

EXAMPLE 2

Transchelation of Zinc Chloride with Sodium Pyrithione In-situ in a Shampoo to Produce Zinc Pyrithione Particles in Platelet Form in the Shampoo 32 g of hydroxypropyl methylcellulose suspending agent was mixed in water (198 ml) and heated to 70° C. for 30 minutes. Zinc chloride (3.4 g) was added to the above mixture. The sodium salt of 2-mercaptopyridine-N-oxide (18.6 g) was added to the above mixture over a period of 5 min. and stirred at 70° C. In a separate container, melted cocoamide DEA was added a mixture of triethanolamine lauryl sulfate, triethanolamine, FD&C yellow no. 5, FD&C blue no. 1 and ethylene glycol distearate. The two mixtures were stirred together at 1500 rpm and the temperature was slowly brought down to ambient. A portion of the shampoo thus formed was analyzed for size and shape of the in-situ generated zinc 2-mercaptopyridine-N-oxide particles. Scanning electron microscopy of the particles showed that these particles had a platelet shape. The median particle size obtained by laser light scattering showed that the particles were present in the form of platelets having a median particle size of 3 $\mu$m, with a distribution of particle sizes in the range of from 0.7 to 10 microns.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for preparing a zinc pyrithione-containing personal care composition which comprises in-situ prepared zinc pyrithione, comprising the step of reacting, in a personal care composition comprising at least one surfactant and having a high viscosity relative to zinc pyrithione in water alone, pyrithione acid or a pyrithione salt other than zinc pyrithione, or a combination thereof, with a zinc compound that is soluble in the personal care composition, said zinc compound being selected from the group consisting of zinc salts of organic acids, zinc salts of inorganic acids, zinc hydroxide, zinc oxide, and combinations thereof, thereby causing in-situ transchelation of the pyrithione acid or pyrithione salt with the zinc salt to form said zinc pyrithione-containing personal care composition, wherein said in-situ prepared zinc pyrithione is stable against settling in said personal care composition.

2. The process of claim 1 wherein said personal care composition is a shampoo comprising water or an alcohol, and at least one surfactant.

3. The process of claim 1 wherein said personal care composition is a soap comprising water or an alcohol, and at least one surfactant.

4. The process of claim 1 wherein said personal care composition is a skin care medicament comprising water or an alcohol, and at least one surfactant.

5. The process of claim 1 wherein said zinc salt is selected from the group consisting of zinc sulfate, zinc chloride, zinc acetate, and combinations thereof.

6. The process of claim 1 wherein said pyrithione salt is selected from the group consisting of magnesium pyrithione, strontium pyrithione, copper pyrithione, cadmium pyrithione, zirconium pyrithione, and combinations thereof.

7. A process for preparing a zinc pyrithione-containing personal care composition selected from the group consisting of shampoo, soap, skin care medicament, and combinations thereof, said process comprising contacting water or an alcohol with at least one surfactant and with a transchelation product produced by reacting pyrithione acid, or a pyrithione salt other than zinc pyrithione that is soluble in the personal care composition, or a combination thereof, with a zinc compound selected from the group consisting of zinc salts of organic acids, zinc salts of inorganic acids, zinc hydroxide, zinc oxide, and combinations thereof, said zinc compound being soluble in the personal care composition, said personal care composition having a high viscosity relative to zinc pyrithione in water alone, and wherein said transchelation product is stable against settling in said personal care composition.

8. The process of claim 7 wherein said zinc salt is selected from the group consisting of zinc sulfate, zinc chloride, zinc acetate, and combinations thereof.

9. The process of claim 7 wherein said pyrithione salt is selected from the group consisting of magnesium pyrithione, strontium pyrithione, copper pyrithione, cadmium pyrithione, zirconium pyrithione, and combinations thereof.

10. A personal care composition comprising:
    (a) water or an alcohol,
    (b) at least one dispersant or surfactant, and
    (c) as an antimicrobial or preservative additive, particles of an in-situ transchelation reaction product of a zinc compound selected from the group consisting of zinc salts of organic acids, zinc salts of inorganic acids, zinc hydroxide, zinc oxide, and combinations thereof, said zinc compound being soluble in said water or alcohol, with pyrithione acid or a pyrithione salt other than zinc pyrithione that is soluble in said water or alcohol wherein said personal care composition has a high viscosity relative to zinc pyrithione in water alone, and wherein said in-situ transchelation reaction product is stable against settling in said personal care composition.

11. The personal care composition of claim 10 wherein said zinc salt is selected from the group consisting of zinc sulfate, zinc chloride, zinc acetate, and combinations thereof.

12. The personal care composition of claim 10 wherein said pyrithione salt is selected from the group consisting of magnesium pyrithione, strontium pyrithione, copper pyrithione, cadmium pyrithione, zirconium pyrithione, and combinations thereof.

13. The personal care composition of claim 10 wherein said component (a) is present in said personal care composition in an amount of from about 5% to about 70%, wherein said component (b) is present in an amount of from about 2% to about 50%, and wherein said component (c) is present in an amount of from about 0.1% to about 2%, based upon the weight of said personal care composition, with the proviso that the total of said component (a) plus said component (b) plus said component (c) not exceed 100%, and wherein said reaction product is in the form of solid particles in said personal care composition, said solid particles being amorphous or crystalline particles in a shape selected from the group consisting of rods, needles, cubes, platelets, and combinations thereof.

14. The personal care composition of claim 10 wherein said surfactant comprises sodium lauryl sulfate, sodium laureth sulfate, or a combination thereof.

15. The personal care composition of claim 10 wherein said alcohol is selected from the group consisting of isopropyl alcohol, benzyl alcohol, ethanol, and combinations thereof.

16. A coated substrate comprising a substrate selected from the group consisting of skin, hair and combinations thereof, and a coating on said substrate, said coating comprising a personal care composition having a high viscosity relative to zinc pyrithione in water alone, and comprising particles of zinc pyrithione and at least one surfactant, said particles being produced by an in-situ transchelation reaction of pyrithione acid or a soluble pyrithione salt other than zinc pyrithione with a zinc compound selected from the group consisting of zinc salts of organic acids, zinc salts of inorganic acids, zinc hydroxide, zinc oxide, and combinations thereof, wherein said zinc pyrithione is stable against settling in said personal care composition.

17. The coated substrate of claim 16 wherein said zinc salt is selected from the group consisting of zinc sulfate, zinc chloride, zinc acetate, and combinations thereof.

18. The coated substrate of claim 16 wherein said pyrithione salt is selected from the group consisting of magnesium pyrithione, strontium pyrithione, copper pyrithione, cadmium pyrithione, zirconium pyrithione, and combinations thereof.

19. The coated substrate of claim 16 wherein said particles of zinc pyrithione have a shape selected from the group consisting of platelets, rods, needles, cylinders, cones, ellipsoids, prisms, parallelepipeds, pyramids, cubes, and combinations thereof.

20. The coated substrate of claim 16 wherein said particles of zinc pyrithione are crystals having a configuration selected from triclinic, monoclinic, orthorhombic, tetragonal, cubic, trigonal, hexagonal now have a shape selected from the group consisting of platelets, rods, needles, cylinders, cones, ellipsoids, prisms, parallelepipeds, pyramids, cubes, and combinations thereof.

21. The composition of claim 10 which additionally comprises a supplemental antimicrobial additive selected from the group consisting of polymyxin E, polymyxin B, lower alkyl esters of para-hydroxybenzoic acid, salts thereof, and combinations thereof.

22. The personal care composition of claim 10, wherein said personal care composition is selected from the group consisting of liquid, gel, or creme shampoos; liquid, gel, or creme skin care medicaments; liquid, gel, or creme soaps, and combinations thereof.

23. The personal care composition of claim 16, wherein said personal care composition is selected from the group consisting of liquid, gel, or creme shampoos; liquid, gel, or creme skin care medicaments; liquid, gel, or creme soaps, and combinations thereof.

* * * * *